United States Patent [19]

Makino et al.

[11] Patent Number: 5,017,564

[45] Date of Patent: May 21, 1991

[54] SOLID PHARMACEUTICAL PREPARATION AND METHOD OF PRODUCING SAME

[75] Inventors: Tadashi Makino, Ibaraki; Koji Doi, Suita; Masayoshi Matsuoka, Habikino; Toshiharu Tsuboi, Settsu, all of Japan

[73] Assignee: Senju Pharmaceutical Co., Ltd., Osaka, Japan

[21] Appl. No.: 360,869

[22] Filed: Jun. 2, 1989

[30] Foreign Application Priority Data

Jun. 3, 1988 [JP] Japan ................................ 63-137925

[51] Int. Cl.[5] ..................... A01N 43/04; A01N 43/78; A61K 9/28; A61K 9/30

[52] U.S. Cl. ........................................ 514/47; 514/46; 514/48; 514/276; 514/960; 424/474; 424/475; 424/498; 424/502

[58] Field of Search ........................... 514/47, 48, 276; 424/474, 475, 476, 498, 502

[56] References Cited

U.S. PATENT DOCUMENTS

| | | | |
|---|---|---|---|
| 2,775,521 | 12/1956 | Matels et al. | 426/72 |
| 3,037,911 | 6/1962 | Stoyle, Jr. et al. | 514/276 |
| 3,308,217 | 3/1967 | Lowy et al. | 514/276 |
| 3,863,633 | 2/1975 | Marta et al. | 128/260 |
| 4,136,162 | 1/1979 | Fuchs et al. | 424/27 |
| 4,208,406 | 6/1980 | Lapinet et al. | 424/180 |
| 4,382,924 | 5/1983 | Berling et al. | 424/180 |
| 4,702,913 | 10/1987 | Marty | 424/95 |
| 4,713,245 | 12/1987 | Ando et al. | 424/438 |
| 4,764,388 | 8/1988 | Sullivan et al. | 426/311 |
| 4,814,171 | 3/1989 | Marty | 424/95 |
| 4,834,985 | 5/1989 | Elger et al. | 424/488 |
| 4,871,718 | 10/1989 | Carniglia | 514/23 |

FOREIGN PATENT DOCUMENTS

| | | | |
|---|---|---|---|
| 0254978 | 2/1988 | European Pat. Off. . | |
| 1431841 | 4/1976 | United Kingdom | 514/276 |

OTHER PUBLICATIONS

Dictionnaire Vidal 1961 p. 1878, Office De Vulgarisation Pharmaceutique, Paris.

Rote Liste 1987, Editio Cantor, Aulendorf Germany.

*Primary Examiner*—Stanley J. Friedman
*Assistant Examiner*—Theodore J. Criares
*Attorney, Agent, or Firm*—Wenderoth, Lind & Ponack

[57] ABSTRACT

Provided are a solid pharmaceutical preparation which contains disodium adenosine triphosphate together with a vitamin $B_1$ salt or the like and a method of treatment of human asthenopia by orally administering the same. Also provided are a solid pharmceutical preparation according to the abovementioned preparation, which further contains a low-melting fat- or oil-like substance and has an improved stability of disodium adenosine triphosphate, and a method of producing the same.

10 Claims, No Drawings

SOLID PHARMACEUTICAL PREPARATION AND METHOD OF PRODUCING SAME

BACKGROUND OF THE INVENTION

1. Field of the Invention

This invention relates to a solid pharmaceutical preparation containing disodium adenosine triphosphate (hereinafter sometimes referred to briefly as "ATP-2Na"), which is useful, for example, in alleviating or treating cerebrovascular disorder, cardiac failure and asthenopia, and a vitamin $B_1$ salt or a vitamin $B_1$ derivative having vitamin B activity, to such solid pharmaceutical preparation stabilized by further addition of a low-melting fat- or oil-like substance, and to a method of producing such composition.

2. Description of Prior Art

Since the discovery by Fiske, Lohmann et al. (1929) of adenosine triphosphate (hereinafter sometimes referred to briefly as "ATP") occurring in muscular tissue infusions, the role of disodium adenosine triphosphate in living organisms has been elucidated step by step by a number of researchers. As a representative of the compounds having the so-called energy rich phosphate bond, ATP is found everywhere in living organisms. The energy required in living organisms is supplied solely by ATP. On the other hand, the clinical use of ATP-2Na as a therapeutic agent has become fairly popular and its efficacy has been established in certain diseases.

On the other hand, vitamin $B_1$ is known to be effective in the treatment of such diseases as beriberi, neurasthenia, neuritis, neuralgia, edema, congestive heart failure and acute circulatory shock and, accordingly, thiamine disulfide and various other derivatives as well as salts thereof, such as hydrochloride and nitrate, have been synthesized.

It is an object of the invention to provide a pharmaceutical composition with the above-mentioned pharmacological effects of ATP-2Na being potentiated or extended as a result of combined use of another pharmacologically active ingredient with ATP-2Na.

In particular, the invention is to provide an ATP-2Na-containing pharmaceutical composition made more effective in the treatment of asthenopia in view of the current situation in which not a few people complain of asthenopia as a result of the popularized use of various kinds of office automation (OA) equipment. ATP-2Na has drawbacks. Thus, in the solid form, it is unstable under high temperature and/or high humidity conditions and, in the form of an aqueous solution or suspension, its stability decreases with the decreasing pH value. Therefore, preparations or dosage forms containing it, particularly tablets, have poor stability as far as ATP-2Na is concerned. The content of the active ingredient in said preparations decreases with the lapse of time and coloration occurs.

In some pharmaceutical compositions containing other ingredients, ATP-2Na strongly interacts with said other ingredients, leading to still more decreased stability. Furthermore, in the case of tablets, crystals are distorted due to the pressure, friction, heat and other effects applied or produced in the step of molding under pressure and as a result, the fall in content with the lapse of time is accelerated in many instances.

Thus, when ATP-2Na is made up into solid pharmaceutical compositions, for example tablets, stability problems arise. Accordingly, it is a further object of the invention to provide a combination drug composition of practical use which contains ATP-2Na and another active ingredient and in which the decomposition of the active ingredient with the lapse of time is inhibited to a sufficient extent and the stability of ATP-2Na thereby improved.

SUMMARY OF THE INVENTION

The present inventors made various investigations in an attempt to create and stabilize combination drug compositions containing ATP-2Na and another pharmacologically active ingredient, as mentioned above, and unexpectedly found that a combination drug composition containing ATP-2Na and a vitamin $B_1$ salt or a vitamin $B_1$ derivative having vitamin $B_1$ activity has markedly increased effect in the treatment of asthenopia and further that addition of a low-melting fat- or oil-like substance to such combination drug composition containing ATP-2Na and a vitamin $B_1$ salt or the like results in marked inhibition of the decomposition of ATP-2Na to give a more stable and more effective pharmaceutical composition. Further investigations based on these findings have now led to completion of the present invention.

Thus the invention is directed to:

(1) A solid pharmaceutical preparation which contains ATP-2Na and a compound selected from a group consisting of vitamin $B_1$ salt and vitamin $B_1$ derivatives having vitamin $B_1$ activity (hereinafter sometimes referred to as vitamin $B_1$ salt or the like) and a method of treatment of human asthenopia by orally administering the same;

(2) A solid pharmaceutical preparation which further contains a low-melting fat- or oil-like substance and the method of producing the same.

The solid pharmaceutical preparation according to the invention which contains ATP-2Na together with a vitamin $B_1$ salt or the like produces better effects in the treatment of asthenopia as compared with the corresponding preparation containing ATP-2Na alone. The solid pharmaceutical preparation according to the invention which further contains, in addition to the combination of ATP-2Na and a vitamin $B_1$ salt or the like a low-melting fat- or oil-like substance can maintain the ATP-2Na content at a high level even after the lapse of a number of days as a result of suppressed degradation of ATP-2Na therein. Thus the invention can provide a more effective therapeutic agent for asthenopia with much increased stability of ATP-2Na.

DETAILED DESCRIPTION OF THE INVENTION

ATP-2Na, which is to be used in the practice of the invention, has the following structure:

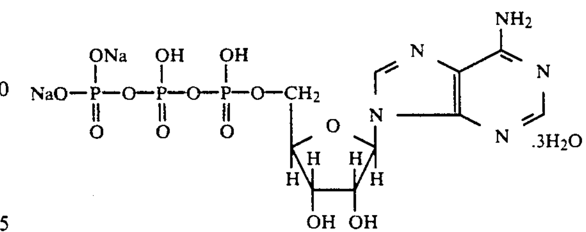

The main reaction involved in the decomposition of this substance is said to be hydrolysis. Thus, the decomposition proceeds from ATP-2Na to ADP (disodium adenosine diphosphate) and then to AMP (disodium adenosine monophosphate). Further decomposition is accompanied by the phenomenon of browning.

As the vitamin $B_1$ salt or the vitamin $B_1$ derivative having vitamin $B_1$ activity, which is to be used in the solid pharmaceutical composition according to the invention, there may be mentioned, among others, vitamin $B_1$ hydrochloride (thiamin hydrochloride), vitamin $B_1$ nitrate (thiamin nitrate), as well as prosultiamine (TPD), fursultiamine (TTFD), dicethiamine, octotiamine, thiamin disulfide, cycotiamine, bisibutiamine, bisbentiamine and benfotiamine, and their salts with acids, for example hydrochloride, nitrate and sulfate.

The low-melting fat- or oil-like substance to be used for the stabilization of the combination drug composition according to the invention may be any of fatty, oily or waxy substances with a relatively low melting point and without producing any unfavorable effect on ATP-2Na, such as, for example, hydrocarbons, higher fatty acids, higher alcohols, polyhydric alcohol fatty acid esters, polyhydric alcohol higher alcohol ethers and alkylene oxide polymers or copolymers. Preferred among these are polyhydric alcohol fatty acid esters, polyhydric alcohol higher alcohol ethers and alkylene oxide polymers or copolymers.

As the hydrocarbons, there may be mentioned, among others, n-alkanes containing 17 to 50 carbon atoms, such as n-heptadecane, n-octadecane, n-nonadecane, n-eicosane, n-heneicosane, n-docosane, n-tricosane, n-tetracosane, n-pentacosane, n-triacontane, n-pentatriacontane, n-tetracontane and n-pentacontane, and mixtures of these (petrolatum, paraffin wax, microcrystalline wax, etc.).

As the higher fatty acids, there may be mentioned, for example, capric acid, lauric acid, myristic acid, palmitic acid, stearic acid, arachidic acid, behenic acid, lignoceric acid, cerotic acid, mixtures of these, and other higher fatty acids derivable from naturally occurring fats and oils.

As the higher alcohols, there may be mentioned lauryl alcohol, myristyl alcohol, cetyl alcohol, stearyl alcohol, arachyl alcohol, mixtures of these, other higher alcohols derivable from naturally occurring oils, and so forth.

As the polyhydric alcohol fatty acid esters, there may be mentioned, for instance, esters derived from an alcohol having two or more hydroxyl groups within the molecule (e.g. alkylene glycol such as ethylene glycol or propylene glycol, polyalkylene glycol such as polyethylene glycol, polypropylene glycol or copolymer of these, saccharide such as sorbitol, sucrose or raffinose, intramolecular dehydration product derived from sorbitol, such as 1,5-sorbitan, 1,4-sorbitol or 3,6-sorbitan, glycerin, diethanolamine, pentaerythritol) and a fatty acid (e.g. acetic acid, propionic acid, butyric acid, pelargonic acid, capric acid, undecylenic acid, lauric acid, tridecylic acid, myristic acid, pentadecylic acid, palmitic acid, heptadecylic acid, stearic acid, nonadecanoic acid, undecylenic acid, oleic acid, elaidic acid, sorbic acid, linoleic acid, linolenic acid, arachidonic acid, stearolic acid), more specifically, sorbitan fatty acid esters having a molecular weight of 400 to 900, such as sorbitan monostearate, sorbitan tristearate, sorbitan monooleate, sorbitan sesquioleate and sorbitan monopalmitate, polyoxyalkylenesorbitan fatty acid esters having a molecular weight of 1,000 to 1,500, such as polyoxyethylenesorbitan tristearate, polyoxyethylenesorbitan monooleate and polyoxyethylenesorbitan tripalmitate, polyoxyalkylenesorbitol fatty acid esters such as polyoxyethylenesorbitol hexastearate, polyoxyethylenesorbitol hexaoleate, polyoxyethylenesorbitol tristearate and polyoxyethylenesorbitol tetralaurate, polyoxyalkylenesorbitol beeswax derivatives such as polyoxyethylenesorbitol beeswax derivatives, polyoxyalkylenelanolin derivatives such as polyoxyethylenelanolin derivatives, propylene glycol fatty acid esters having a molecular weight of 200 to 700, such as propylene glycol monopalmitate, propylene glycol monostearate, propylene glycol dilaurate, propylene glycol dimyristate, propylene glycol dipalmitate and propylene glycol distearate, and ethylene glycol fatty acid esters having a molecular weight of 500 to 1,200, such as ethylene glycol monolaurate, ethylene glycol palmitate, ethylene glycol margarate, ethylene glycol stearate, ethylene glycol dilaurate, ethylene glycol dimyristate, ethylene glycol dipalmitate and ethylene glycol dimargarate, other alkylene glycol fatty acid esters, polyoxyalkylene-castor oil derivatives having a molecular weight of 3,500 to 4,000, such as polyoxyethylenecastor oil derivatives, polyoxyalkylene fatty acid esters having a molecular weight of 1,900 to 2,200, such as polyoxyethylene stearate, polyoxyethylene oleate, polyoxyethylene palmitate and polyoxyethylene linoleate, glycerin mono-fatty acid esters having a molecular weight of 300 to 600, such as glycerin monoacetate, glycerin monopropionate, glycerin monostearate, glycerin monooleate, glycerin monopalmitate and glycerin monolinoleate, sucrose fatty acid esters having a molecular weight of 400 to 1,300, such as sucrose monolaurate, sucrose monomyristate, sucrose monopalmitate, sucrose monostearate, sucrose trimysristate, sucrose tripalmitate and sucrose tristearate, and so forth.

As the polyhydric alcohol higher alcohol esters, there may be mentioned ethers derived from a polyhydric alcohol (as mentioned above as the alcohol component of the polyhydric alcohol fatty acid esters) and higher fatty alcohol (e.g. cetyl alcohol, stearyl alcohol, oleyl alcohol, octyl alcohol, decyl alcohol). More specifically, those usable in many instances are, for example, polyoxyethylene higher alcohol ethers such as polyoxyethylene lauryl ether, polyoxyethylene cetyl ether, polyoxyethylene stearyl ether, polyoxyethylene oleyl ether, polyoxyethylene octyl ether and polyoxyethylene decyl ether, and polyoxypropylene-polyoxyethylene higher alcohol ethers such as polyoxypropylene-polyoxyethylene cetyl ether, polyoxypropylenepolyoxyethylene stearyl ether, polyoxypropylene-polyoxyethylene oleyl ether, polyoxypropylene-polyoxyethylene octyl ether and polyoxypropylene-polyoxyethylene lauryl ether.

As the alkylene oxide polymers, those having a molecular weight of 1,000 to 10,000 (e.g. polyethylene glycol 6000) may be used. As the alkylene oxide, there may be mentioned, among others, ethylene oxide, propylene oxide, trimethylene oxide and tetrahydrofuran.

As the alkylene oxide copolymers, copolymers of two or more of the alkylene oxides mentioned above and having a molecular weight of 1,000 to 10,000 may be used.

Of these low-melting fat- or oil-like substances those having a melting point of about 20° to 90° C. may generally be used. Ones having a melting point of 20° to 60° C. are particularly preferred. These low-melting fat- or oil-like substances may be used either singly or in the form of a mixture of two or more of them.

The combination drug composition according to the invention contains a vitamin $B_1$ salt or a vitamin $B_1$ derivative having vitamin $B_1$ activity in an amount of about 0.01 to 5 parts by weight, usually about 0.1 to 2 parts by weight, preferably about 0.1 to 1 part by weight, on the vitamin $B_1$ (thiamin) basis, per part by weight of ATP-2Na.

The combination drug composition according to the invention is advantageously used as a solid pharmaceutical preparation. The term "solid pharmaceutical preparation" as used herein means solid drug preparations in the form of tablets, granules, powders, capsules and so forth.

The solid combination pharmaceutical preparations according to the invention can be produced in a conventional manner.

Generally, they can be produced by coating enteric coated tablets containing ATP-2Na with a vitamin $B_1$ salt or a vitamin $B_1$ derivative having vitamin $B_1$ activity or admixing enteric coated tablets containing ATP-2Na with a vitamin $B_1$ salt or the like.

Furthermore, in manufacturing such combination drug composition, it is desirable for the stabilization of ATP-2Na in said composition to incorporate in said composition a low-melting fat- or oil-like substance such as mentioned above. In that case, generally, a low-melting fat- or oil-like substance is admixed with ATP-2Na, the resulting mixture is molded under pressure, and the thus-obtained solid pharmaceutical composition is coated or admixed with a vitamin $B_1$ salt or a vitamin $B_1$ derivative having vitamin $B_1$ activity. Also in producing such stabilized combination drug composition, the solid preparation containing ATP-2Na should desirably be in the form of enteric coated tablets. The latter are then suitably coated or admixed with a vitamin $B_1$ salt or the like. The coating with a vitamin $B_1$ salt or the like is generally carried out with convenience by the dry coating technique using it in the granular or granulated form or by incorporating a vitamin $B_1$ salt or the like into a sugar coating layer.

More specifically, when one or more of the above-mentioned low-melting fat- or oil-like substances are incorporated into the combination drug composition according to the invention, these low-melting fat- or oil-like substances are added, either in the solid form or in the liquid form, to ATP-2Na. When they are added in the solid form (as a powder), the low-melting fat- or oil-like substances are used in an amount of at least 0.1 part by weight, generally about 0.1 to 3 parts by weight, preferably about 0.2 to 1 part by weight, per part by weight of ATP-2Na. When they are added in the liquid form (as a solution), the low-melting fat- or oil-like substances are used in an amount of at least 0.1 part by weight, generally about 0.1 to 3 parts by weight, preferably 0.2 to 0.8 part by weight.

Generally, the stabilized solid combination drug compositions according to the invention are produced by admixing a low-melting fat- or oil-like substance such as mentioned above to ATP-2Na and then subjecting the resulting mixture to a step of molding under pressure. The admixing is effected by any means of admixing commonly used in producing pharmaceutical preparations, for example by blending, kneading, comalaxating, sieving or agitating. For instance, it is possible to add the low-melting fat- or oil-like substance directly to ATP-2Na and to blend the materials (addition in powder form), or a solvent may be added and the materials blended, kneaded, granulated and dried by conventional methods. Alternatively, it is also possible to dissolve the low-melting fat- or oil-like substance in an appropriate solvent, admix the solution with ATP-2Na uniformly and knead, granulate and dry, or treat otherwise, the resulting mixture by conventional methods (addition in solution form). Usable as said appropriate solvent for the addition in solution form are, for example, water, dimethylformamide, acetone, ethanol, propyl alcohol, isopropyl alcohol, butyl alcohol, methylene chloride, trichloroethane and other solvents which will not exert any unfavorable effect on ATP-2Na. After achieving uniform admixture, the resulting composition can be molded under pressure by a known method to give ATP-2Na-containing solid pharmaceutical compositions. The term "molding under pressure" as used herein means compression under pressure to give a desired shape or form and, in most cases, said term means tableting, among others. Presumably, the incorporation of said low-melting fat- or oil-like substances results in decreased strain of crystals in the step of molding under pressure and, furthermore, in improved moldability, so that a lower pressure becomes sufficient for the molding purposes. In the process for producing the solid pharmaceutical preparation according to the invention, one or more of various additives known to be usable in solid-form preparations may be added as desired in an appropriate step or steps. Thus, for example, excipients or carriers such as crystalline cellulose (e.g. Avicel PH101, Asahi Chemical Industry), celluloseglycolic acid calcium salt, corn starch, wheat starch, lactose, sucrose, glucose, calcium sulfate, calcium phosphate, sodium chloride, etc., binders such as gum arabic, gelatin, methylcellulose, polyvinylpyrrolidone, hydroxypropylcellulose (hereinafter sometimes referred to briefly as "HPC"), hydroxypropylmethylcellulose, etc., lubricants such as magnesium stearate, talc, synthetic aluminum silicate, sodium lauryl sulfate, boric acid, magnesium oxide, paraffin, etc., colorants, flavors, corrigents, and the like may be added.

Furthermore, since ATP-2Na is unstable to acids, it is desirable, as mentioned above, to subject the ATP-2Na-containing composition according to the invention to enteric coating to prevent the decomposition of ATP-2Na in gastric juice. The enteric coating can be performed by any per se known method. Usable coating materials for such purpose are those generally used as enteric coating materials, for example, cellulose acetate phthalate, hydroxypropylmethylcellulose phthalate, hydroxymethylcellulose acetate succinate, carboxymethylcellulose, methacrylic acid-acrylic acid copolymers [e.g. Eudragit L30D-55 (Rohm, West Germany)], shellac, polyethylene glycol, polysorbates (e.g. Tween 80), polyoxyethylene-polyoxypropylene glycol (e.g. Pluronic F68), castor oil, triacetin, talc, and colorants such as titanium oxide and red iron oxide.

The solid pharmaceutical preparation according to the invention may be sugar-coated. The sugar-coated tablets can be produced by any known coating technique using a conventional coating agent or composition. Usable as such coating composition are, for example, sugar coating compositions prepared by using granulated sugar, talc, pullulan, powdered gum arabic (acacia), crystalline cellulose, etc.

The combination drug composition according to the invention which contains ATP-2Na and a vitamin $B_1$ salt or the like may further contain one or more other pharmacologically active ingredients as desired. As the pharmacologically active ingredients just mentioned, various substances capable of enhancing and/or expanding the pharmacological efficacy of the solid pharmaceutical preparations of this invention may be used. As such other pharmacologically active ingredients, there may be mentioned, for example, vitamin $B_2$, vitamin $B_6$, vitamin $B_{12}$, vitamin A, vitamin C, vitamin E, l-menthol, caffeine, cyclandelate, parotin, medicines for the stomach and intestines, such as sodium bicarbonate and gentian, and flavors for such medicines. These may be used either alone or in combination. Such other pharmacologically active ingredients may be used in an amount of about 0.00000005 to 20 parts by weight, preferably about 0.000001 to 10 parts by weight, although the amount should be varied depending on the kind of each ingredient and on the purpose for which it is used.

Pharmaceutical compositions additionally containing such other pharmacologically active ingredients can be manufactured, for example, by coating or admixing enteric coated tablets containing ATP-2Na with said ingredients separately from or together with a vitamin $B_1$ salt or the like.

The solid pharmaceutical preparations obtained in the above manner by incorporating a low-melting fat- or oil-like substance in a combination drug composition comprising ATP-2Na and a vitamin $B_1$ salt or a vitamin $B_1$ derivative having vitamin $B_1$ activity and, if desired, by further adding one or more other additives are stable and effective and show no changes in appearance (browning etc.), with the decomposition during storage as resulting from the molding under pressure being inhibited.

The solid combination pharmaceutical preparation according to the invention is particularly suited for use as a therapeutic agent for asthenopia. It is administered at a daily dose of about 0.7 to 7.0 mg/kg, preferably about 2 to 3 mg/kg, as ATP-2Na.

The daily dose of the vitamin $B_1$ salt or vitamin $B_1$ derivative having vitamin $B_1$ activity is about 0.2 to 5 mg/kg, preferably about 0.4 to 2.0 mg/kg.

Examples

The following examples will illustrate the invention in further detail but are by no means limitative of the scope of the invention.

EXAMPLE 1

Using a fluidized bed granulator (Fuji Sangyo model FD-3S), the ingredients indicated in the formulation a) shown below were mixed up and the resultant mixture was granulated and dried. The granular composition thus obtained was sieved, supplemented with the ingredients indicated below under b) (magnesium stearate etc.) and, after mixing up, tableted on a tableting machine using a 4.5 R punch (6.0 mm $\phi$) at a pressure of 1.0 ton/$cm^2$ to give tablets each weighing 90 mg.

The plain tablets thus obtained were subjected to enteric coating with an aqueous suspension containing Eudragit L30D-55, Tween 80, polyethylene glycol 6000 and talc according to the formulation c) shown below, using Accela Coater 24 (Manesty), and then to sugar coating using granulated sugar, talc, pullulan, etc., together with fursultiamine hydrochloride according to the formulation d) shown below, to give sugar-coated tablets.

| Material | | Per tablet |
|---|---|---|
| Plain tablet | | |
| (a) ATP-2Na | | 22.0 mg |
| Lactose | | 53.5 |
| Corn starch | | 10.0 |
| HPC | | 2.5 |
| (Water) | | (43.7 μl) |
| | Subtotal | 88.0 |
| (b) Corn starch | | 1.5 |
| Magnesium stearate | | 0.5 |
| | Total | 90.0 mg |
| Enteric coated tablet | | |
| (c) Plain tablet | | 90.0 mg |
| Eudragit L30D-55 | | 23.0 (6.9 as solids) |
| Tween 80 | | 0.7 |
| Polyethylene glycol 6000 | | 0.3 |
| Talc | | 2.1 |
| (Water) | | (23.0 μl) |
| | Total | 100.0 mg |
| Sugar coated tablet | | |
| (d) Enteric coated tablet | | 100.0 mg |
| Fursultiamine hydrochloride | | 10.9 |
| Titanium oxide | | 1.0 |
| Pullulan PI-20 | | 0.8 |
| Avicel PH 101 | | 0.8 |
| Talc | | 52.8 |
| Granulated sugar | | 43.7 |
| (Water) | | (20 μl) |
| | Total | 210.0 mg |

Test for Efficacy on Asthenopia

Subjects

Twenty persons who had been working at the VDT (video display terminal) for at least 1 hour per day on the average and had complained of asthenopia, other than those whose asthenopia was thought to be due to other causes than the operations at the VDT as a result of ophthalmologic examination, were clinically given the tablets of Example 1 (hereinafter referred to as "tablets A") and the efficacy of said tablets was evaluated on the basis of the subjective symptoms reported by the subjects.

Method of Administration

The subjects were divided into two groups (each 10 subjects). The first group was given two tablets A three times a day consecutively for 2 weeks. The 10 subjects of the second group, which served as a control group, were given tablets prepared in the same manner as in Example 1 except that fursultiamine was replaced with the same quantity of granulated sugar, namely tablets containing 22 mg of disodium adenosine triphosphate alone as the active ingredient (hereinafter referred to as "tablets B"), in the same manner as mentioned above. After said two weeks, the treatments of the first and the second group were switched from one to the other; thus, tablets B were administered to the first group and tablets A to the second group consecutively for 2 weeks in the same manner.

Results Summarized

After completion of the administration, the extents of improvement in subjective symptoms as reported by all the subjects gave the following distribution:

Persons who reported better improvement with tablets A than with tablets B...12 persons;

Persons who reported no significant difference in improvement between tablets A and tablets B...8 persons;

Persons who reported better improvement with tablets B than with tablets A...none.

Conclusion

It can be seen from the above test results that administration of tablets A subjectively alleviated asthenopia. Thus it can be concluded that tablets A are useful in relieving asthenopia.

EXAMPLE 2

Using a fluidized bed granulator (Fuji Sangyo model FD-3S), the ingredients of the formulation a) shown below, in which Polyethylene glycol 6000 was used as the low-melting fat- or oil-like substance, were mixed and the resultant mixture was sprayed with an aqueous solution of hydroxypropylcellulose (binder solution) and granulated, and dried. The granular composition thus obtained was sieved, then supplemented with the ingredients mentioned below under b) (magnesium stearate etc.) and tableted on a tableting machine (Kikusui Seisakusho model Correct 19K) using a 4.5 R punch (6.0 mm ϕ) at a pressure of 1.0 ton/cm$^2$ to give tablets each weighing 90 mg.

The plain tablets thus obtained were subjected to enteric coating with an aqueous suspension containing Eudragit L30D-55, Tween 80, polyethylene glycol 6000 and talc according to the formulation c) shown below, using Accela Coater 24 (Manesty), and then to sugar coating using granulated sugar, talc, pullulan, etc., together with fursultiamine hydrochloride according to the formulation d) shown below. The solid pharmaceutical preparation thus obtained was tested for storage stability. The results obtained are shown in the table given below.

Results of storage stability testing

| Item | Invention |
|---|---|
| Initial | (100%) |
| After storage at 60° C. for 1 week | 95% |
| After storage at 40° C. for 4 weeks | 95% |

| Material | | Per tablet |
|---|---|---|
| Plain tablet | | |
| (a) ATP-2Na | | 22.0 mg |
| Lactose | | 47.5 |
| Corn starch | | 10.0 |
| Polyethylene glycol 6000 | | 6.0 |
| HPC | | 2.5 |
| (Water) | | (43.7 μl) |
| | Subtotal | 88.0 mg |
| (b) Corn starch | | 1.5 |
| Magnesium stearate | | 0.5 |
| | Total | 90.0 mg |
| Enteric coated tablet | | |
| (c) Plain tablet | | 90.0 mg |
| Eudragit L30D-55 | | 23.0 |
| | | (6.9 as solids) |
| Tween 80 | | 0.7 |
| Polyethylene glycol 6000 | | 0.3 |
| Talc | | 2.1 |
| (Water) | | (23.0 μl) |
| | Total | 100.0 mg |
| Sugar coated tablet | | |
| (d) Enteric coated tablet | | 100.0 mg |
| Fursultiamine hydrochloride | | 10.9 |
| Titaniaum oxide | | 1.0 |
| Pullulan PI-20 | | 0.8 |
| Avicel PH 101 | | 0.8 |
| Talc | | 52.8 |
| Granulated sugar | | 43.7 |
| (Water) | | (20 μl) |
| | Total | 210.0 mg |

In the storage stability testing, the residual content of ATP-2Na after the lapse of each storage period was determined by liquid chromatography and expressed in terms of percent residue.

The solid pharmaceutical preparation according to the invention was found to have improved stability with respect to ATP-2Na even under severe storage conditions.

EXAMPLE 3

Core tablets (4.5 mm ϕ, 5 R) were produced according to the formulation a) shown below by following the procedure of Example 2 and then subjected to enteric film coating according to the formulation b) shown below to give enteric core tablets. Then, the tablets and a powder mixture (external layer composition) containing fursultiamine hydrochloride which was prepared according to the formulation c) shown below using a fluidized bed granulator were processed into multiple compressed tablets on a tableting machine for manufacturing multiple compressed tablets (Kikusui Seisakusho model Correct 45 DC) using a 6.5 R punch (8.5 mm ϕ) at a tableting pressure of 1.0 ton/cm$^2$. These tablets were subjected further to film coating using hydroxypropylmethylcellulose and other ingredients according to the formulation d) shown below. The solid pharmaceutical preparation obtained was tested for storage stability in the same manner as in Example 2. The results obtained are shown in the table given below.

| Material | | Per tablet |
|---|---|---|
| Core tablets | | |
| (a) ATP-2Na | | 22.0 mg |
| Lactose | | 14.8 |
| Corn starch | | 3.0 |
| Polyethylene glycol 6000 | | 3.0 |
| HPC | | 1.0 |
| (Water) | | (19 μl) |
| | Subtotal | 43.8 |
| Magnesium stearate | | 0.2 |
| | Total | 44.0 mg |
| Enteric coated core tablet | | |
| (b) Core tablet | | 44.0 mg |
| Eudragit L30D-55 | | 13.3 |
| | | (8.0 as solids) |
| Tween 80 | | 0.8 |
| Talc | | 1.2 |
| (Water) | | (13.3 μl) |
| | Total | 50.0 mg |
| Multiple compressed tablet | | |
| (c) Enteric coated core tablet | | 50.0 mg |
| Fursultiamine hydrochloride | | 10.9 |
| Lactose | | 86.0 |
| Corn starch | | 30.0 |
| β-Cyclodextrin | | 30.0 |
| HPC | | 4.5 |
| (Water) | | (85.5 μl) |
| | Subtotal | 161.4 |
| Avicel PH 101 | | 30.0 |
| Magnesium stearate | | 0.6 |
| | Total | 242.0 mg |
| Film-coated multiple compressed tablet | | |
| (d) Multiple compressed tablet | | 242.0 mg |
| Hydroxypropylmethylcellulose | | 5.8 |
| Polyethylene glycol 6000 | | 1.0 |
| Titanium oxide | | 1.2 |

-continued

| Material | Per tablet |
| --- | --- |
| (Water) | (58.7 μl) |
| Total | 250.0 mg |

Results of storage stability testing

| Item | Invention |
| --- | --- |
| Initial | (100%) |
| After storage at 60° C. for 1 week | 97% |
| After storage at 40° C. for 4 weeks | 100% |

The above test results indicate that the solid pharmaceutical preparation according to the invention which contains a low-melting fat- or oil-like substance has very good stability as far as the content of ATP-2Na is concerned.

What is claimed is:

1. A solid pharmaceutical preparation in solid dosage unit form which contains disodium adenosine triphosphate and a compound selected from the group consisting of vitamin $B_1$ salt and vitamin $B_1$ derivatives having vitamin $B_1$ activity in an amount of 0.01 to 5 parts on vitamin $B_1$ basis per part by weight of disodium adenosine triphosphate.

2. A solid pharmaceutical preparation according to claim 1, which further contains a low-melting fat- or oil-like substance having a melting point of 20° to 90° C. in an amount of about 0.1 to 3 parts, per part by weight, of disodium adenosine triphosphate.

3. A solid pharmaceutical preparation according to claim 2, wherein the low-melting fat- or oil-like substance is a substance selected from the group consisting of hydrocarbons, higher fatty acids, higher alcohols, polyhydric alcohol fatty acid ester, polyhydric alcohol higher alcohol ethers and alkylene oxide polymers or copolymers.

4. A solid pharmaceutical preparation according to claim 1, 2 or 3, wherein the preparation is in the form of tablets, granules, powders or capsules.

5. A solid pharmaceutical preparation according to claim 1, 2 or 3, which is to serve as a therapeutic agent for human asthenopia, wherein the selected compound is fursultiamine or a salt thereof.

6. A solid pharmaceutical preparation according to claim 5, wherein the selected compound is fursultiamine hydrochloride.

7. A method for the treatment of human asthenopia comprising orally administering to a human suffering from asthenopia a solid pharmaceutical preparation in solid dosage unit from which contains disodium adenosine triphosphate and a compound selected from the group consisting of vitamin $B_1$ salt and vitamin $B_1$ derivatives having vitamin $B_1$ activity in an amount of 0.01 to 5 parts on vitamin $B_1$ basis per part by weight of disodium adenosine triphosphate.

8. A method for the treatment of asthenopia according to claim 7, wherein the daily doses of disodium adenosine triphosphate and the selected compound are from about 0.7 to 7 mg and from about 0.2 to 5 mg, respectively, per kg body weight of the human suffering from asthenopia.

9. A method for the treatment of asthenopia according to claim 7 or 8, wherein the selected compound is fursultiamine or a salt thereof.

10. A method for the treatment of asthenopia according to claim 9, wherein the selected compound is fursultiamine hydrochloride.

* * * * *